United States Patent
Sharma et al.

(10) Patent No.: US 6,730,838 B1
(45) Date of Patent: May 4, 2004

(54) **OPIUMLESS AND ALKALOID-FREE NON-NARCOTIC OPIUM POPPY (*PAPAVER SOMNIFERUM*) VARIETY "SUJATA"**

(75) Inventors: Jawahar Ram Sharma, Lucknow (IN); Raj Kishori Lal, Lucknow (IN); Ajai Prakash Gupta, Lucknow (IN); Hari Om Misra, Lucknow (IN); Vasudha Pant, Lucknow (IN); Ram Chandra, Lucknow (IN); Mohd Rashid, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/276,720

(22) Filed: Mar. 26, 1999

(30) Foreign Application Priority Data

Feb. 12, 1999 (IN) ......................................... 233/DEL/99

(51) Int. Cl.$^7$ ............................. A01H 1/00; A01H 5/00
(52) U.S. Cl. ....................... 800/323; 435/410; 530/370; 800/295; 800/260; 800/298; 800/276; 800/270
(58) Field of Search .................................. 800/323, 298, 800/276, 270, 295, 260; 435/410; 530/370

(56) References Cited

U.S. PATENT DOCUMENTS 6,067,749 A * 5/2000 Fist et al. .................... 47/58.1

OTHER PUBLICATIONS

Ghiorghita et al. Revue Romanie de Biochimie, vol. 2, No. 4, pp. 279–286, 1984.*
Nyman. Herditas, vol. 93, pp. 121–124, 1980.*
Singh et al. Journal of Genetics and Breeding. vol. 52, pp. 301–306, 1998.*

* cited by examiner

Primary Examiner—Phuong T. Bui
(74) Attorney, Agent, or Firm—Birch, Stewart, Kolasch & Birch, LLP

(57) ABSTRACT

The present invention relates to an opiumless and alkaloid-free non-narcotic opium poppy designated as var. Sujata having the following morphological/argonomic features:

| | |
|---|---|
| Days to 50% flowering | 100–105 |
| Plant height (cm) | 80–100 |
| Peduncle length (cm) | 18–20 |
| Peduncle colour | Patchy-black |
| No. of capsules/branches per plant | 3–4 |
| Capsule shape | Flat |
| Capsule surface | ~glabrous (white bloom +) |
| No. of stigmatic rays per capsule | 10–12 |
| Shape and size of stigmatic rays | slightly small, flattened |
| Latex-flow on incision | Absent |
| Seed count per gram of weight | 3040–3310 |
| Seed colour | Dull-white |
| Seed shape | Reniform |
| Seed size | Bold (Thickness ++) |
| Seed yield (g/m$^2$) | 120–140 |
| Straw yield (g/m$^2$) (Capsule hulls) | 135–150 |
| Opium alkaloids in straw | Absent. |

6 Claims, 1 Drawing Sheet

(1 of 1 Drawing Sheet(s) Filed in Color)

Plants with lanced capsules

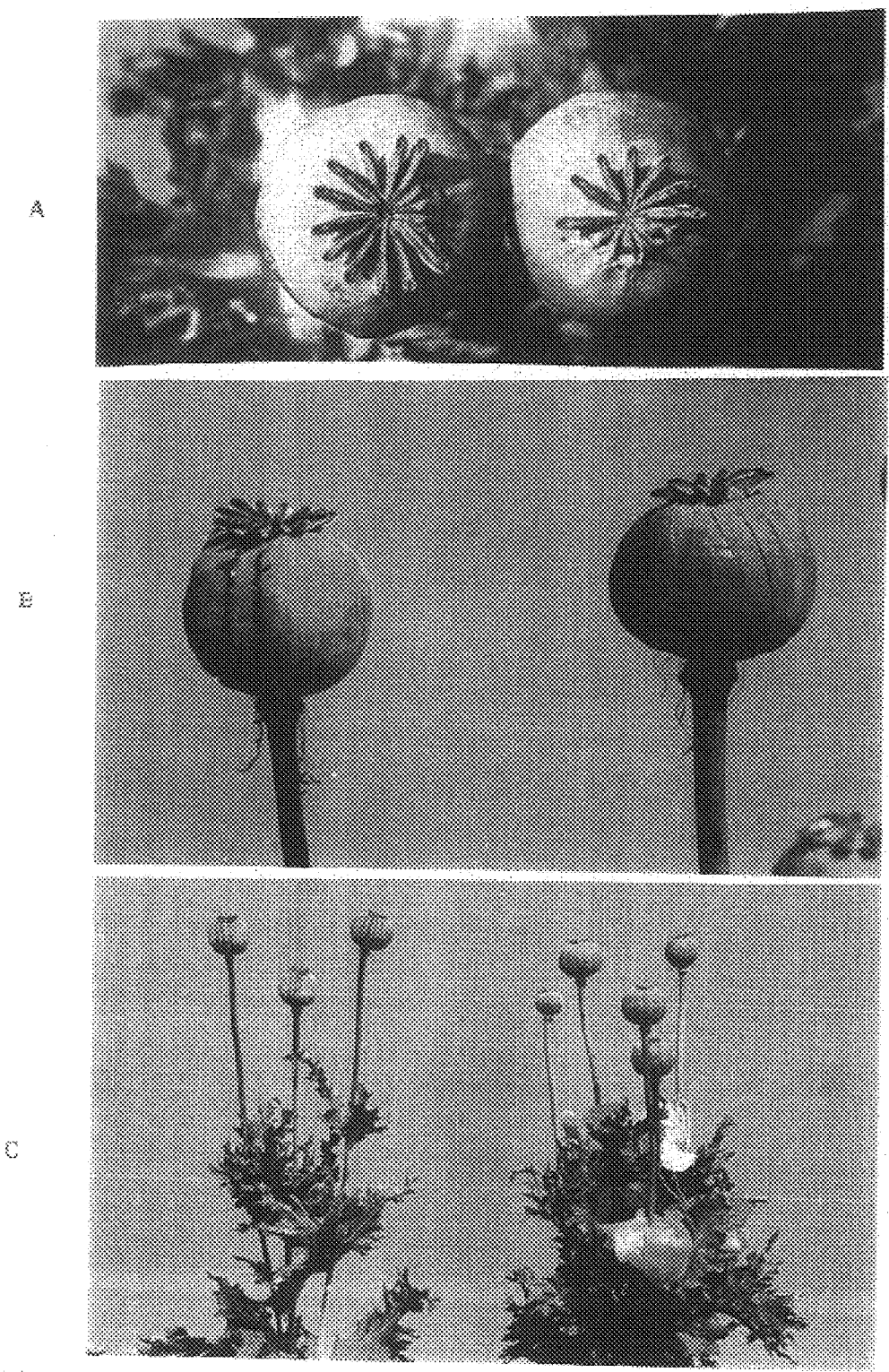
Fig. 1 – Presence of latex in normal parent Mees-2B (Left) and absence in LL-34 (Right) of opium poppy:
A – Ray-Plucking in capsules
B – Lancing (incision) of capsules
C – Plants with lanced capsules

OPIUMLESS AND ALKALOID-FREE NON-NARCOTIC OPIUM POPPY (*PAPAVER SOMNIFERUM*) VARIETY "SUJATA"

FIELD OF THE INVENTION

The present invention relates to an opiumless and alkaloid-free non-narcotic opium poppy (*Papaver somniferum*) designated as var. Sujata.

BACKGROUND OF THE INVENTION

An opiumless and alkaloid-free non-narcotic var. Sujata of opium poppy has been developed by induced mutagenesis (mutation breeding) in an otherwise narcotic (with opium and opium alkaloids both) strain Mass-2B of opium poppy. The var. Sujata is also attributed with high yield of seeds which are rich in protein and oil content both. As such, the variety offers a cheap and permanent means of combating opium-linked abuses across the world. Besides, it also offers a nutritious food item (seed) of high caloric value and largely unsaturated vegetable oil which might serve as a dietary control of coronary heart problem.

Opium poppy is commercially cultivated in a large number of countries, such as Tasmania (Australia), Turkey, Austria, Holland, Poland, Romania, Germany, Sweden, Netherlands, Greece, Portugal, Italy, France, Spain, erstwhile USSR, Yugoslavia, Slovakia, Bulgaria, India, China, Iran, Iraq, Afganistan, Pakistan, Thailand, Laos, Myanmar, etc. covering an area of around 270,000–300,000 ha. across the world. However, based on official records of the International Narcotic Control Board (INCB), Vienna, the area under poppy cultivation way only 37000–56000 ha. (1989–1993) for licit production of opium. Poppy cultivation in India covered 29,799 ha during 1996 for legal production of opium.

However, since opium and opium alkaloids, particularly morphine are addictively narcotic; their illicit production and illegal transactions have perpetuated over centuries worldover. As a consequence, INCB which regulates the opium poppy cultivation in the world, has permitted all the poppy growing countries, except India (with strict licensing system and vigilence exercised by the Narcotic Control Bureau. Govt. of India) to cultivate only straw (CPS) varieties for seeds and not for opium. But these CPS varieties are not free from opium which can be collected by unscrupulous growers for illegal users. Hence, there was a need always fell to combat opium-linked social abuses which has now assumed a serious proportion at global level. Around 17 million people all over the world are opium addicts and about half as much to heroin—a chemical derivative of morphine which is the major component of opium. Development of a plant-type (CPS variety) with neglegible or no narcotic alkaloids in poppy straw was therefore suggested by Liersch and Krzymanski (Postap. Nauk. Rolniezych. Vol. 40/45: 99–100, 1993). Genetic and chemical investigations in Germany revealed that CPS vars. Soma (Sweden) and Przenkc (Poland) had morphine content as low as 0.01% in straw (capsule hulls), and a new cross-bred line RM 9/95 possessed even less than 0.01% morphine, which conforms to the requirement of the German Federal Health Agency (Nothnagel et al., Proc. Intern. Symp. Breeding Research on Medicinal and Aromatic Plants, Jun. 30–Jul. 4, 1996, Quedlinburg, Germany, pp. 120–123). In India also, an accession CIMAP-OP1 was reported to have low alkaloids (0.05% morphine, 0.001% codeine, 0.051% thebaine, 0.13% papaverine and 0.087% narcotine) in straw (Bajpai et al., Plant Breed, Vol. 115: 425, 1996). But again, these strains with low morphine accumulation in straw are not devoid of opium. They can be lanced (incision of the ripe capsule) to collect opium for illegitimate exploitation. The novel approach is therefore to invent and develop an opiumless and alkaloid-free variety of opium poppy which can serve as a cheap and permanent means to control opium abuses across the world.

Furthermore poppy seeds are rich in protein and minerals hence a good source of energy with caloric value 100 g=2050 KJ (cf. Te'te'nyl, Horticulture Reviews, Vol. 19: 373, 1997). As such, they are widely used as an additive, especially in fish curry, in a soft drink—Thandai and in Posta-Halva (a delicious sweet dish) and in confectionary/bakery. Poppy seeds also have some anti-carcinogenic property as reflected by experimental search (Aruna, Food Chem. Toxicol. 30: 11, 1992; Burger, Burger's Medicinal Chemistry, Part II. A Wiley Interscience Publication, 1140, 1979).

Iranians consider the poppy seeds aphrodisiac, constipating and tonic due to the presence of fatty acids, minerals, enzymes, etc. (Nergiz and Oties, J. Sci. Food Agr. 66: 117, 1994).

Still further, poppy seeds contain high proportion of (edible) vegetable oil which is rich in unsaturated faty acids, particularly oleic acid and linoleic acid (Wealth of India: Raw Materials Vol. 7: 234 & 246, 1966). The latter tends to lower down the blood cholesterol in human beings (of Singh et al., Indian J. agric. Sci. 60: 358, 1990), hence poppy seed oil might be useful as a dietary control of coronary heart disease in human beings. The linoleic acid is also the precursor of prostaglandins which maintain skin-growth, kidney-function and fertility (Burger, Burger's Medicinal Chemistry, Part II. A Wiley Interscience Publication, 1140, 1979). Besides, poppy oil is also used against diarrhoea, dysentry and scalds. It is also extensively used for culinary purposes and salad dressing. Several other uses of poppy seeds and oil have been reported by Te'te'nyl (Horticulture Reviews, Vol. 19: 373, 1997).

However, production of such valuable poppy seeds and seed-oil both has always been restricticted due to lack of a non-narcotic which can be extensively cultivated safely without any risk of the opium and opium alkaloids involved in drug trafficking. Therefore, it also calls for inventing and developing a non-narcotic poppy variety—virtually a 'seed poppy' which is not only opiumless and alkaloid-free, but also a high yielder of seeds containing high proportion of protein and particularly unsaturated fatty acids in its oil.

OBJECT OF THE INVENTION

The main object of the present invention is, therefore, to develop an opiumless and alkaloid-free (non-narcotic) variety of opium poppy (*P. somniferum* L.) which can provide a cheap and permanent solution to the problems of opium-linked social abuses across the world.

Another object of the present invention is to genetically improve the seed-yield potential (*Posta dana/Khus-Khus*) which is impressively rich in protein hence a highly nutritive food component of high caloric value.

Still another object is to select for genetically enhanced capacity of seeds to synthesize more oil content which is largely unsaturated, hence may serve as a natural dietary control of coronary heart disease and a viable supplement to production of vegetable oil in the country.

DETAILED DESCRIPTION OF THE INVENTION

Accordingly, the present invention provides an opiumless and alkaloid-free non-narcotic opium poppy designated as var. Sujata characterized by the following morphological/agronomic features:

| | |
|---|---|
| Days to 50% flowering | 100–105 |
| Plant height (cm) | 80–100 |
| Peduncle length (cm) | 18–20 |
| Peduncle colour | Patchy-black |
| No. of capsules/branches per plant | 3–4 |
| Capsule shape | Flat |
| Capsule surface | ~glabrous (white bloom +) |
| No. of stigmatic rays per capsule | 10–12 |
| Shape and size of stigmatic rays | slightly small, flattened |
| Latex-flow on incision | Absent |
| Seed count per gram of weight | 3040–3310 |
| Seed colour | Dull-white |
| Seed shape | Reniform |
| Seed size | Bold (Thickness ++) |
| Seed yield (g/m$^2$) | 120–140 |
| Straw yield (g/m$^2$) (Capsule hulls) | 130–150 |
| Opium alkaloids in straw | Absent |

The invention further provides an opiumless and alkaloid-free non-narcotic opium poppy designated as var. Sujata with 20.8 to 23.9% total seed protein.

The invention further provides an opiumless and alkaloid-free non-narcotic opium poppy designated as var. Sujata comprising the following oil content and composition:

| | |
|---|---|
| Oil content in seeds (%) | 50–52 |
| Palmitic acid 16:0 (%) | 12 |
| Oleic acid 18:1 (%) | 19 |
| Linoleic acid 18:2 (%) | 56 |

The invention further provides a method for the development of an opiumless and alkaloid-free non-narcotic opium poppy designated as var. Sujata by induced mutagenesis which comprises:

(a) Selecting two high yielding opium varieties as parental materials designated as C1 and C2 for treatment with both physical and chemical mutagens;

(b) Preparing eight samples containing at least 100 seeds of each of the C1 and C2 parents;

(c) irradiating five samples of both C1 and C2 with gamma rays ($^{80}$Co) at 10, 20, 40, 60 and 80 kR doses;

(d) Treating the 6th sample with 0.4% aqueous ethyle methane sulfonate (EMS) alone and subjecting the 7th sample to combined treatment of gamma radiation at 20 kR dose followed by 0.4% treatment with aqueous EMS in both C1 and C2;

(e) Leaving the 8th sample in each of the two parents—C1 and C2 untreated to be used as 'control';

(f) Growing all the 8 samples including 'control' of both C1 and C2 parents in paired rows forming M1 generation and selfing 15–20 plants by bagging in each of the treatments including 'controls' in both parents before flowering;

(g) Collecting selfed seeds on maturity in C1 and C2 based on phenotypic appearance and disease resistance separately for each treatment;

(h) Raising the seeds in step (g) in plant-to-progeny rows forming M2 generation alongwith interspersed paired rows of parental controls;

(i) Subjecting the matured capsules formed 15–20 days after flowering in each and every plant of the M2 families and the two parental 'contro' to 'Ray-Pluck Method' for rapid examination of the presence or absence of latex oozing out on plucking a ray or two of the capsule;

(j) identifying the latexless (LL) and partial latex (PL) plants in each of the M2 families using 'Ray-Pluck Method' and collecting the open pollinated seeds of LL and PL plants separately;

(k) Raising the suspected LL/PL mutant genotypes/plants again in plant-to-progeny (paired) rows forming M3 families together with paired rows of the two controls in M3 generation and selfing all the plants by bagging in each of the M3 families before the commencement of flowering;

(l) Repeating 'Ray-Pluck Method' in all the suspected M3 families and isolating the M3 families relating to combined treatment of C1 with confirmed LL and PL mutant genotypes/plants followed by collecting separately selfed seeds of all the LL/PL plants on maturity;

(m) Re-confirming the LL/PL plants by 'Ray-Pluck Method' and increasing their genetic purity through selfing/inbreeding by growing them again in plant-to-progeny (multiple)rows along with variable rows of C1 control (M4 generation) followed by collecting selfed seeds separately on maturity.

The invention provides a further method for identifying latexless/partial latex opium poppy variety which comprises plucking of one or two astigmatic rays located on the top of the capsule of a plant to observe the flow or oozing out of latex, the said method being called as 'Ray-Pluck Method'.

In an embodiment of the invention, the parental material comprises the strain Mass-2B as C-1 and var. Shweta as C-2 in the development of opiumless and alkaloid-free non-narcotic opium poppy designated as var. Sugata.

In another embodiment of the invention, treatment with physical mutagen comprises gamma radiation in the development of an opiumless and alkaloid-free non-narcotic opium poppy designated as var. Sujata.

In another embodiment of invention, the treatment with chemical mutagen comprises the treatment with ethyl methane sulfonate in the development of an opiumless and alkaloid-free non-narcotic opium poppy designated as var. Sujata.

In yet another embodiment of the invention, screening for the presence or absence of latex (raw opium) in capsule comprises a 'Ray-Pluck Method' in the development of an opiumless and alkaloid-free non-narcotic opium poppy designated as var. Sujata.

In a further embodiment of the invention, the invention further provides an opiumless and alkaloid-free non-narcotic opium poppy designated as var. Sujata comprising the seeds deposited at NCIMB Ltd, U.K., bearing the accession Provisional accession No.41009.

Var. Sujata has been developed through special effort of mutation breeding, representing genetic transformation of narcotic 'opium poppy' into a non-narcotic 'seed poppy'. Being opiumless and alkaloid-free, var. Sujata offers a cheap and permanent means of combating opium-like social abuses across the world. Besides, as it is non-narcotic, it can be safely grown as a food crop, the seeds of which are very nutritious due to high proportion of protein therein. Also, its seeds contain high percentage of oil which is largely unsaturated due to high proportions of oleic and linoleic acids. Hence, it is a very healthy edible oil providing a natural dietary control of coronary heart disease caused by high blood cholesterol. Thus, var. Sujata is definitely of great utility of human beings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 1A–1C Presence of latex in normal parent Mass-2B (Left) and absence in LL-34 (Right) of opium poppy;

1A—Ray-Plucking in capsules,

1B—Lancing (incision) of capsules,

1C—Plants with lanced capsules.

TAXONOMIC DESCRIPTION OF VAR. SUJATA

The var. Sujata is an erect growing herb of around 100 cm. height with a few branches. Leaves are radical having irregular lobe with prominently dented margins. Surface of stem and leaves is mildly coated with white bloom (+) in contrast to a little more bloom (++) in the parental control, Mass-2B (C1). Flowers are solitary on slightly longer peduncle than C1. Petals are four, white with smooth margin. Stemans are numerous, arranged in whorl. Stigma is capitate with 10–12 stigmatic rays which are smaller and a bit flattened compared to 12–14 long and nearly slender stigmatic rays in the C1. The fruit is a capsule which is flat in shape and normally glabrous against the waxy (white powder, ++) surface of C1. The peduncle which bears the capsule is slightly longer and patchy black (on maturity) compared to the uniform black peduncle of C1.

Seeds are reniform (kidney-shaped), very small, dull-white and similar in size to the C1. Seed count per gram of weight is 3040–3310 in Sujata and 4410–4520 in the C1 (Mass-2B).

In brief, some of the argomonic and morphological distinguishing characteristics of var. Sujata in comparison to its parent—Mass 2B(C1) are listed in Table 2.

TABLE 2

Morphological/agronomic features of var. Sujata against the parent C1 (Mass-2B) of opium poppy

| Morphological/agronomic features | Var. Sujata | Mass-2B |
|---|---|---|
| Days to 50% flowering | 100–105 | 100–104 |
| Plant height (cm) | 80–100 | 85–110 |
| Peduncle length (cm) | 18–20 | 15–18 |
| Peduncle colour | Patchy-black | Uniform black |
| No. of capsules/branches per plant | 3–4 | 3–4 |
| Capsule shape | Flat | Flat |
| Capsule surface | ~glabrous (white bloom +) | Waxy (white bloom ++) |
| No. of stigmatic rays per capsule | 10–12 | 12–14 |
| Shape and size of stigmatic rays | slighty small, flattened | Long, nearly slender |
| Latex flow on incision | Absent | Profuse |
| Seed count per gram of weight | 3040–3310 | 4410–4520 |
| Seed colour | Dull-white | Off-white |
| Seed shape | Reniform | Reniform |
| Seed size | Bold (Thickness ++) | Medium bold (Thickness +) |
| Seed yield (g/m$^2$) | 120–140 | 100–130 |
| Straw yield (g/m$^2$) (Capsule hulls) | 130–150 | 100–120 |

(Method of development of var. Sujata (Breeding programme)

The new var Sujata has been evolved by induced mutagenesis in opium poppy. The process of its development is elaborated below in successive steps:

Two elite lines/varieties of opium poppy, namely Mass-2B (C1) and Shweta (C2) giving high yields of latex (opium) and opium alkaloids were selected as parental materials for treatment with both physical (gamma radiation) and chemical (ethyl methane sulfonate-EMS) mutagens.

(ii) Eight samples each comprising 100 seeds were prepared in both C1 and C2 parents (Total 16 samples).

(iii) Five samples of both C1 and C2 were irradiated with gamma rays ($^{60}$Co) at 10,20,40,60 and 80 kR doses.

(iv) The 6$^{th}$ sample was treated with 0.4% aqueous EMS alone, while the 7$^{th}$ sample was subjected to combined treatment of gamma radiation at 20 kR dose followed by 0.4% treatment with aqueous EMS in both C1 and C2.

(v) The 8$^{th}$ sample in each of the two parents—C1 and C2 were left untreated to be used as 'control'.

(vi) All the 8 samples (7 treated+1 control) of both C1 and C2 parents were grown in paired rows (M1 generation). Before flowering, 15–20 plants in each of the treatments in both parents were selfed by Bagging. Parents were also selfed similarly. On maturity, selfed seeds of 115 plants in C1 and 42 plants in C2 (total 157 plants based on phenotypic appearance and disease resistance) were collected separately for each treatment.

(vii) All the 157 plants were raised in plant-to-progeny (paired) rows (now called M2 families) along with interspersed paired rows of parental controls (M2 generation).

(viii) Around 15–20 days after flowering, when capsules were ready/matured, each and every plant of the 157 M2 families and the two parental controls were subjected to 'Ray-Pluck Method' (see later) especially devised for rapid examination of the presence/absence of latex oozing on plucking a ray or two of the capsule.

(ix) Out of the thousands of plants in different M2 families, 1–3 plants in only 5 families (3 families at 10 kR of C2 and one each at combined treatment of C1 and C2 both) were found to be latexless (LL), i.e. no oozing out of latex on ray-plucking. Besides, 1–2 plants in other 6 families (2 each at EMS alone and combined treatment of C1 and 2 at combined treatment of C2) had partial latex (PL), i.e. oozing out watery or very diluted latex. Thus, in total, 19 plants were suspected (?) to the LL/PL in 11 M2 families. On maturity, open-pollinated seeds of all the 19 LL/PL plants (?) in 11 M2 families were collected separately.

(x) All the 19 suspected LL/PL mutant genotypes/plants were again raised in plant-to-progeny (paired) rows (19 M3 families) together with paired rows of the two controls (M3 generation). Nearly all the plants in each of the 19 M3 families were selfed by bagging before the flowering commenced.

(xi) Repeated the same exercise (ray-plucking) elaborated in point No. (viii) earlier, in all the suspected 19 M3 families. Finally, only 3 M3 families relating to combined treatment of C1 were found to possess 31LL and 23 PL mutant genotypes/plants. This confirmed the genetic control of LL/PL status of the selected plants. On maturity, selfed seeds of all the 54 LL/PL (31 LL+23 PL) plants were collected separately.

(xii) To re-confirm LL/PL plants and also to increase their genetic purity (homozygosity) by selfing/inbreeding, 28 LL and 23 PL plants (3 LL plants were rejected due to capsule rot) were again grown in plant-to-progeny (multiple) rows (total 51 LL/PL families) along with variable rows of C1 control (M4 generation). Before the flowering occurred, nearly all the plants in each of the 51 LL/PL families were selfed by bagging.

(xiii) Repeated the same exercise (ray-plucking) as described in point No. (viii) earlier, in all the 51 LL/PL families in M4 generation.

(xiv) Observations for LL/PL nature in M4 generation revealed the following two facts:

All the PL plants eventually turned to be LL at maturity of the capsules. In fact, mostly lateral capsules (which are younger than the main capsule) secreted watery fluid or very diluted latex on 'ray-pluck'. But as soon as they reached maturity stage, their fluid dried up showing no secretion on ray-pluck.

About 60–95% of plants in some LL/PL families were LL; though some families had lower frequencies also. The three families, namely LL-14, PL-24 and LL-34 possessed 88, 94 and 95% LL genotypes. Thus, a very high degree of homozygosity (genetic purity) for latexlessness was achieved in M4 generation and the genetic control of LL nature was double confirmed. Hopefully, nearly 100% homozygosity shall be achieved by M6 generation.

The best opiumless strain, LL-34 was designated as var. Sujata.

'Ray-Pluck Method' of rapid screening

Fast detection and rapid screening of a massive number of plants (in thousands) for the presence or absence of latex (raw opium) in M2 generation cannot be achieved by the common procedure of lancing (incision/scarification) of the capsules with Nashtar/Nurnee (a special kind of knife with 4 blades). This is very comberous and time-consuming procedure, not suitable for rapid screening. To overcome this difficulty, a novel 'Ray-Pluck Method' was devised for the first time, which was very fast in detecting latexless (LL) or partial latex (PL) genotypes without resorting to the normal lancing of capsules in opium poppy. This method entails plucking of one or two stigmatic rays located on the top of the capsule and looking for the flow or oozing out of latex. The ray-pluck method has been depicted vis-a-vis the lancing of capsules in FIG. 1. Had this procedure not been devised, it was utterly difficult to fast screen the enormous size of populations for LL genotypes.

Stability of LL-34 (var. Sujata)

The var. Sujata was evaluated and confirmed for its non-narcotic nature (opiumless and straw alkaloid-free) over three generations (M2, M3 and M4) under the northern sub-tropical conditions of Lucknow, Uttar Pradesh where opium poppy in grown in large area. Hence, var. SUGATA is stable for its qualitative trait of opiumlessness. However, its quantitative traits, like seed yield and oil content may vary due to genotype x environment interaction, as is common in all seed and oil drops.

Chemical analysis of poppy-straw for opium alkaloids

The five major opium alkaloids, namely morphine, codeine, thebaine, papaverine and narcotine are concentrated in large measures in the opium and in small amounts in the poppy-straw (dried capsule hulls, after removing the seeds). However, as the opium in the LL plants was absent, the 5 alkaloids were determined by TLC densitometric procedure of Gupta and Verma (Indian J. Pharm. Sci. Vol. 58:161, 1966) in the powdered capsule hulls of 22 representative LL/PL plants of the two M3 families (both belonging to combined treatment of C1). The procedure involved scanning of silica gel plates 60 F254 (Merck, Darmstadt, Germany) after color visualization using Dragendorff reagent No. 11C. The densitometric scanning profiles of the 5 opium alkaloids were calibrated against the corresponding standards and quantified. Morphine, codeine and narcotine were absent in all the LL/PL genotypes; while papaverine was present in traces in all but 5 genotypes and thebaine in none except two. Thus, 5 LL/PL genotypes were completely free from opium alkaloids in their straw. The best mutant genotype LL-34 (now strain LL-34) is compared against the parent C1 (Mass-28) and a standard straw cv. Sanchita in Table 3 below. The same pattern was also noticed in the M4 generation.

Table 3. Alkaloids in poppy-straw of strain LL-34 (Sujata) compared to Mass-2B (parent) and cv. Sanchita

TABLE 3

Alkaloids in poppy-straw of strain LL-34 (Sujata) compared to Mass-2B (parent) and cv. Sanchita

| Genotypes | Opium | Opium alkaloids (%)** | | | | |
|---|---|---|---|---|---|---|
| | | Mo | Co | Th | Pa | Na |
| LL-34 (Sujata) | – | – | – | — | – | – |
| Mass-2B ® | ++ | 0.550 | 0.035 | t | 0.095 | t |
| Sanchita* | ++ | 1.05 | 0.12 | 0.03 | 0.12 | 0.07 |

® vide Govt. Alkaloids Works, Neemuch
*vide Bajpai et al. Plant Breed. 115: 425, 1996
**Mo, Co, Th, Pa and Na are, in order, Morphine, Codeine, Thebaine, Papaverine and Narcotine; – nil; ++ present; t traces Evaluation of seed weight and seed protein After removing the capsule-hull, weight of seeds (g/capsule) was determined by an electronic balance in the M3 generation for 22 representative LL/PL plants. But in M4 generation, seed weight ($g/m^2$) of 11 LL/PL families was determined for 1 m row length in each family. In both generations, seed weght of parental control C1 and an improved cv. Sanchita was also recorded accordingly for comparison.

Further, in the M4 generation, total seed protein was also determined in 13 LL/LP genotypes along with the controls, C1 and cv. Sanchita by micro-kjeldahl method, wherein protein is 6.25 times of the nitrogen (N) estimated in the seed. Results of the best strain LL-34 for both average seed yield and total seed protein are presented in Table 4 along with those for the parental control, C1 (Mass-2B) and cv. Sanchita.

Table 4. Seed yield and total seed protein of L-34 (Sujata) against controls

TABLE 4

Seed yield and total seed protein of LL-34 (Sujata) against controls

| | Seed weight/yield | | Total seed protein |
|---|---|---|---|
| Genotypes | M3 (g/capsule) | M4 ($g/m^2$) | M4 (%) |
| LL-34 (Sujata) | 5.66 | 130 | 23.9 |
| Mass-2B (Parent) | 3.39 | 115 | 22.3 |
| cv. Sanchita | 3.39 | 120 | 20.8 |

Determination of seed oil content and fatty acid composition

Oil content (%) in dried seeds of seven LL/PL genotypes in M3 and 13 LL/PL genotypes in M4 along with that in C1 (Mass-2B) and cv. Sanchita controls was determined by a pulsed NMR (Nuclear Applications in Agricultural Research, NRL, IARI, New Delhi, pp. 9–28, 1994).

Further, the fatty acid composition, particularly the unsaturated fatty acids of 11 LL/PL genotypes together with the two controls, C1 (Mass-2B) and cv. Sanchita, was also determined by gas liquid chromatography (GLC) after converting the non-volatile state of their total fatty acids (oil) into volatile state. The findings on both seed oil content (%) and the composition for the best strain LL-34 versus the two controls C1 (Mass 2B) and cv. Sanchita is shown in Table 5.
Table 5. Oil content and composition of LL-34 (Sujata) against controls

| Content and composition of oil | LL-34 | Mass-2B | Sanchita |
|---|---|---|---|
| Oil content in seeds (%) | 50–52 | 48–50 | 47–49 |
| Palmitic acid 16:0 (%) | 12 | 24 | 8 |
| Oleic acid 18:1 (%) | 19 | 19 | 16 |
| Linoleic acid 18:2 (%) | 56 | 6 | 65 |

Advantages of the present invention

The main advantages of the present invention are:

1. The novel var. Sujata of opium poppy is non-narcotic, i.e. free from opium and opium-alkaloids both. Hence, it offers a cheap and permanent solution to opium and morphine-linked social abuses all over the world. Indeed, it might be the harbinger of world-peace.
2. Being a high seed yielder and non-narcotic, var. Sujata can be grown extensively as seed crop without any risk (no opium, no alkaloids) for producing highly nutritive poppy seeds rich in protein. Poppy seeds are also reported to have anti-carcinogenic property.
3. As its seeds possess high oil content, var. Sujata might prove to be a viable oil-seed crop which can supplement the production of vegetable oil in the country. Furthermore, its oil is largely unsaturated, hence useful as a natural dietary control for coronary heart disease caused by high blood cholesterol in human being. Besides, the poppy oil is also useful against diarrhoea, dysentry and scalds. Furthermore, its largest component linoleic acid is the precursor of prostaglandins which tend to maintain skin-growth, kidney-function and fertility.

What is claimed is:

1. A method for the development of an opiumless and alkaloid-free non-narcotic opium poppy plant by induced mutagenesis, comprising the steps of:
   (a) selecting two high yielding opium varieties as parental materials designated as C1 and C2 for treatment with both physical and chemical mutagens;
   (b) preparing eight samples containing at least 100 seeds of each of the C1 and C2 parents;
   (c) irradiating five samples of C1 and C2 with gamma rays at 10,20,40,60 and 80 kR doses, respectively;
   (d) treating a sixth sample with 0.4% aqueous ethyl methane sulfonate (EMS) and subjecting a seventh sample to combined treatment of gamma radiation at 20 kR dose followed by 0.4% treatment with aqueous EMS in both C1 and C2;
   (e) leaving an eighth sample in each of the two parents, C1 and C2, untreated to be used as controls:
   (f) growing all the eight samples including controls of both C1 and C2 parents in paired rows forming a M1 generation and selfing 15–20 plants in each of the treatments including controls in both parents before flowering;
   (g) collecting selfed seeds on maturity in C1 and C2 based on phenotypic appearance and disease resistance separately for each treatment;
   (h) raising the seeds collected in step (g) in plant-to-progeny rows forming a M2 generation along with interspersed paired rows of parental controls;
   (i) subjecting the matured capsules formed 15–20 days after flowering in each and every plant of the M2 families and the two parental controls to examination of the presence or absence of latex oozing out on plucking a ray or two of the capsule;
   (j) identifying the latexless (LL) and partial latex (PL) plants in each of the M2 families by examination of the presence or absence of latex oozing out on plucking a ray or two of the capsule, and collecting the open pollinated seeds of LL and PL plants separately;
   (k) raising the suspected LL/PL mutant genotypic plants again in plant-to-progeny (paired) rows forming M3 families together with paired rows of the two controls in the M3 generation and selfing all the plants in each of the M3 families before the commencement of flowering;
   (l) repeating examination of the presence or absence of latex oozing out on plucking a ray or two of the capsule in all of the suspected M3 families and isolating the M3 families relating to combined treatment of C1 with confirmed LL and PL mutant genotypic plants followed by collecting separately selfed seeds of all of the LL and PL plants on maturity; and
   (m) re-confirming the LL and PL plants by examination of the presence or absence of latex oozing out on plucking a ray or two of the capsule and increasing their genetic purity through selfing and/or inbreeding by growing them again in plant-to-progeny (multiple) rows along with variable rows of C1 control (a M4 generation) followed by collecting selfed seeds separately on maturity.

2. The method of claim 1, wherein the physical mutagen is gamma radiation.

3. The method of claim 1, wherein the chemical mutagen is ethyl methane sulfonate.

4. An opiumless and alkaloid-free non-narcotic opium poppy plant designated as variety Sujata having NCIMB Number 41009, and having the following characteristics:
   a) 100–105 days to 50% flowering;
   b) plant height of 80–100 cm;
   c) patchy black peduncle having a length of 18–20 cm;
   d) 3–4 capsules/branches per plant;
   e) flat and glabrous capsules;
   f) 10–12 small and flattened stigmatic rays per capsule;
   g) 3040–3310 seed count per gram of weight;
   h) dull white seeds with reniform shape;
   i) seed yield of 120–140 g/m$^2$;
   j) straw yield of 130–150 g/m$^2$;
   k) absence of Opium alkaloids in the straw; and
   l) no latex flow on incision.

5. The opiumless and alkaloid-free non-narcotic opium poppy plant of claim 4 wherein said plant comprises 20.8 to 23.9% total seed protein.

6. The poppy plant of claim 4, wherein the seeds exhibit oil content and composition:
   a) 50–51% oil content in seeds;
   b) 12% palmitic acid (16:0);
   c) 19% oleic acid (18:1); and
   d) 56% linoleic acid (18:2).

* * * * *